(12) United States Patent
Klaassen

(10) Patent No.: US 11,678,868 B2
(45) Date of Patent: Jun. 20, 2023

(54) KIT FOR COLLECTING AND SAMPLING URINE

(71) Applicant: DAKLAPACK EUROPE B.V., Lelystad (NL)

(72) Inventor: Dave Willem Klaassen, Ermelo (NL)

(73) Assignee: DAKLAPACK EUROPE B.V., Lelystad (NL)

( * ) Notice: Subject to any disclaimer, the term of this patent is extended or adjusted under 35 U.S.C. 154(b) by 1109 days.

(21) Appl. No.: 16/098,650

(22) PCT Filed: May 3, 2017

(86) PCT No.: PCT/NL2017/050282
§ 371 (c)(1),
(2) Date: Nov. 2, 2018

(87) PCT Pub. No.: WO2017/192039
PCT Pub. Date: Nov. 9, 2017

(65) Prior Publication Data
US 2019/0142394 A1 May 16, 2019

(30) Foreign Application Priority Data
May 3, 2016 (NL) ..................................... 2016726

(51) Int. Cl.
*A61B 10/00* (2006.01)
*G01N 33/48* (2006.01)
*B01L 3/00* (2006.01)

(52) U.S. Cl.
CPC ........ *A61B 10/007* (2013.01); *A61B 10/0096* (2013.01); *B01L 3/505* (2013.01); *B01L 3/5082* (2013.01); *G01N 33/48* (2013.01)

(58) Field of Classification Search
CPC ... A61B 10/007; A61B 10/0096; A61B 5/208; A61B 5/20; A61B 2560/0431;
(Continued)

(56) References Cited

U.S. PATENT DOCUMENTS 5,569,225 A 10/1996 Fleury
6,235,010 B1 5/2001 Wilkinson et al.
(Continued)

OTHER PUBLICATIONS

International Search Report, issued in PCT/NL2017/050282, dated Aug. 11, 2017.
(Continued)

*Primary Examiner* — Devin B Henson
(74) *Attorney, Agent, or Firm* — Birch, Stewart, Kolasch & Birch, LLP

(57) ABSTRACT

A urine collecting and sample kit includes a self-standing urine collecting bag and an evacuated test tube. The collecting bag includes a female connector fitment adapted to connect to a sample end of the evacuated test tube to enable taking a urine sample from urine deposited in the bag using the evacuated test tube. The female connector fitment is sealed by means of a sealing technique to a front and/or back panel of the self-standing urine collecting bag, at a height above a bottom panel of the bag, such that the insert opening of the fitment faces outward and the sample end of the test tube can be inserted into the recess and be removed from the recess while the bag is in its standing position.

16 Claims, 5 Drawing Sheets

(58) Field of Classification Search
CPC ......... A61B 5/207; A61B 5/154; B01L 3/505; B01L 3/5082; G01N 33/48; A61F 2013/15146; A47K 13/08; A01K 23/00; A01K 23/005
See application file for complete search history.

(56) References Cited

U.S. PATENT DOCUMENTS

| | | | |
|---|---|---|---|
| 8,491,855 B2* | 7/2013 | Yong | A61B 10/0045 |
| | | | 422/547 |
| 2002/0132369 A1 | 9/2002 | Wilkinson | |
| 2004/0116828 A1 | 6/2004 | White, Jr. | |
| 2005/0032239 A1 | 2/2005 | Katz | |
| 2011/0094319 A1 | 4/2011 | Yong | |
| 2014/0338289 A1* | 11/2014 | Coleman | G01N 1/10 |
| | | | 222/92 |

OTHER PUBLICATIONS

Written Opinion of the International Searching Authority, issued in PCT/NL2017/050282, dated Aug. 11, 2017.

* cited by examiner

KIT FOR COLLECTING AND SAMPLING URINE

This invention relates to a kit for collecting and sampling urine, the kit comprising a collecting container and sample tube.

As part of the medical diagnosis it may be required to obtain a urine sample from a person. In some instances the sample can be obtained by the person urinating in a cup and taking the sample from the contents of the cup. However, in some instances a useful sample requires collecting urine over a prolonged period of time, typically over a twenty-four hour period, and taking a sample from the collected urine.

For sampling urine, typically a kit comprising a container, such a as cup, and a sampling device, such as a test tube. The container is used for collecting urine, and the sampling device is used for taking a sample from the collected urine.

When collecting urine over a prolonged period of time, the overall volume of collected urine donations is large compared to single donation. Furthermore, the collected urine needs to be shaken or stirred prior to taken the sample. Therefore, the urine is collected in a container that can be closed between the donations of urine, and that enables shaking of the container without spillage of its contents. Typically a rigid plastic cup with lid is used for collecting the urine. To obtain a sample an evacuated test tube or syringe type device is connected with the cup via an opening in the lid or in the bottom of the cup. See for example: US2011094319, US2002132369, U.S. Pat. No. 6,235,010 for single donation collection containers.

Known collecting devices typically are bulky, which prohibits efficient storage and transport. This is in particular a drawback when collecting of urine over a prolonged period of time is required. Typically a person will use such a kit at home, which requires distribution of the kit, or for the kit to be collected for example at the physician office and taken home by the person. Therefore a compact kit is beneficial since it allows for easy transport, e.g. distribution by mail or to be carried in a coat pocket.

It is noted that foldable and flexible cups are known also, these are however typically fit for receiving a single donation of urine, and do not have the volume and closure that allows for repeatedly donating urine over a prolonged period of time.

Also known are bag type urine collectors, these are however for professional use, i.e. to be used in combination with a catheter and/or which require a syringe with an attached hypodermic needle for taking a sample from the contents of the bag. These types of bags do not allow for collecting urine by directly urinating in the bag, and are to be used in a professional environment, such as a hospital.

It is an object of the current invention to provide an improved kit for collecting urine of a single person over a prolonged period of time, i.e. for collecting multiple donations of urine of a single person over a time period of for example 24 hours, and for taking a sample from the collected urine.

It is a further object of the invention to provide a compact kit comprising a sealable container that is foldable to facilitate storage, transport and distribution.

It is a further object of the invention to provide a compact kit that is easy to use by a non-professional for taking a urine sample.

According to a second aspect, the invention furthermore provides a female connector fitment as disclosed herein, i.e. a fitment configured to be sealed, to one or more panels of a plastic collecting bag, to facilitate obtaining a sample from the contents of the collecting bag, and to enable using an evacuated test tube for taking the sample, wherein the female connector fitment is preferably configured to enable a compact collecting bag. Use of evacuated test tubes is beneficial since it allows for a clean transfer, i.e. without spillage, dripping, etc, of liquid into the test tube.

In an embodiment, the female connector fitment has two sealing surfaces, located on opposite sides of a recess for receiving the sample end of the test tube, to enable the fitment to be sealed between a front panel and a back panel of the sample bag, more in particular to enable the fitment to be sealed to both the front panel and the back panel, such that the fitment extends substantially parallel to the front panel and the back panel of the collecting back contributing to an overall flat configuration of the collecting bag.

In an alternative embodiment, the female connector fitment has a single sealing surface, extending perpendicular to a central axis of the recess for receiving the sample end of a test tube, for sealing the fitment in an opening in a panel of the collecting bag.

The invention therefore provides a urine collecting and sample kit according to claim 1.

A urine collecting and sample kit, according to the invention, comprises:

a self-standing urine collecting bag, having a top portion and a bottom portion; and an evacuated test tube having bottom end and an opposite sample end, the sample end being provided with a pierceable closure, wherein the self-standing urine collecting bag comprises:
a front panel and a back panel, the front panel and the back panel each having a top edge, a bottom edge, opposite side edges, an inside surface and an outside surface, which front panel and back panel meet each other at the opposite side edges with their inside surfaces facing each other;
a collecting opening adapted to enable urinating in the bag, which collecting opening is located at the top portion of the collection bag, and which collecting opening is provided with a fluid tight closure device for repeatedly fluid tight closing sealing of the collecting opening
a bottom panel, located between the front panel and the back panel at the bottom end of the bag, which bottom panel provides support for the front panel and back panels so that, when filled with urine, the urine collection bag is self-supporting and can maintain a stable vertical standing position when resting on a substantially horizontal support surface;
a female connector fitment adapted to connect to a sample end of an evacuated test tube to enable taking a urine sample from urine deposited in the bag using the evacuated test tube, the fitment comprising:
a recess for receiving the sample end of the test tube, the recess having an insert opening for inserting the sample end into the recess, and
a piercing member, located within the confines of the recess such that it not extends outside said recess, the piercing member having a tip for piercing the pierceable closure of the test tube when the sample end of said test tube is inserted into the recess of the female connector,
a sample channel extending between an exit opening at the tip of the piercing member, and an inlet opening at a part of the connector fitment located in the interior of the bag, via which sample channel urine deposited in the interior of the bag can flow from the interior of the bag into the test tube having its sample end inserted into the connector part; and a flexible sealing sleeve, provided around the piercing member, which sealing sleeve seals the exit opening to prevent leakage via the sample channel, and which sealing sleeve strips up along the piercing element when the sample end of the test tube is inserted into the recess to unseal the exit opening, and wherein the connector fitment is sealed by means of a sealing technique to the front and/or back panel, at a height above the bottom panel, such that the connector port faces outward and the sample end of the test tube can be inserted into the recess and be removed from the recess while the bag is in its standing position.

Thus, the invention provides a kit for collecting urine of a single person over a prolonged period of time, i.e. for collecting multiple donations of urine of a single person over a time period of for example 24 hours, and for taking a sample from the collected urine, the kit comprising a flexible collecting bag, which allows for taking a sample using an evacuated test tube while the bag is standing in an upright position. The kit according to the invention thus enables a non-professional to collect urine and take a sample with reduced risk of spillage during the collecting of the donations and when taking the sample.

Therefore, the invention provides a compact kit that is easy to use by a non-professional for collecting sampling urine.

Also, the invention thus provides a compact kit comprising a sealable collecting container that is foldable to facilitate storage, transport and distribution.

Furthermore, the use of plastic sheet material enables low cost production of the bags which is in particular beneficial since these bags are single use only. Also, after the sample has been taken, the bag can be emptied and discarded without taking up much volume in the garbage disposal.

Thus, the invention provides an improved kit for collecting urine of a single person over a prolonged period of time, i.e. for collecting multiple donations of urine of a single person over a time period of for example twenty-four hours, and for taking a sample from the collected urine.

In an embodiment, the collecting bag is configured to hold a volume of urine of at least 2.5 litre, preferably of at least 3 litre, for example 3.5 litre, to thus allow for twenty four hours urine collecting using the same bag.

In an alternative embodiment, a urine collecting and sample kit according to the invention can also comprise a small volume bag, for example for 100 or 200 ml bags, including the female connector fitment, to be used for sampling single urine donations. When the fitment is located between the front panel and the back panel and is sealed to the inside surfaces of the front panel and the back panel at their side edges or at their top edges, the female connector fitment according to the invention extends along the front and the back panel.

In an embodiment, the collecting bag comprises a collecting opening member, preferably obtained by the injection moulding technique, which collecting opening member is sealed between the front panel and the back panel at the top edges thereof, and wherein the collecting opening of the bag is provided in the collecting opening member. Thus, the collecting opening member is defined by the collecting opening member, which in turn is sealed between the front and back panel of the bag. Providing an injection moulded collecting opening member allows for integrating the closure device, or parts thereof, in said member. For example, the member can be provided with screw thread for cooperating with a screw cap, or a hinged cap can be injection moulded as an integral part with the member.

In an embodiment, the fluid tight closure device can be configured as a stop or cap that is clicked, preferably screwed, into a closure position, in which closure position it seals of the collecting opening. Such a closure device is preferably combined with an injection moulded collecting member as disclosed above. For example, in an embodiment the collecting opening member and the stop are provided with screw thread or a bayonet fitting, for securing the stop in the collecting opening.

In an embodiment, the stand-up collecting bag is made of a heat-sealable or weldable plastic sheet material, the sheet material forming the front panel, the back panel and the bottom panel. It is submitted that standing bags as such are known. In a typical standing bag configuration a gusseted bottom panel is sealed between the bottom ends of a front and back panel. In an alternative embodiment the front panel, back panel and the bottom panel are part of a single blank that is folded and sealed into the bag configuration. In yet another embodiment, the front panel and the back panel are part of a single blank and the bottom part is a separate, which blanks are combined to from the standing bag. Also, the standing bag according to the invention may comprise more panels than only a front panel, a back panel and a bottom panel. For example side panels may be provided between the front panel and the back panel to provide a standing bag with a more box like configuration.

Typically, the plastic sheet panels have edge margins disposed along one or more of their edges at which the panels are sealed, in a fluid-tight manner, to other panels and/or to inserts, such as the female fitment or a collecting opening member according to the invention.

In an embodiment, the back panel, the front panel and the bottom panel are made of a foldable a multiple layer plastic sheet material, for example a two-layer compound sheet material, which multiple layer sheet material is configured for enabling heat sealing or welding the components of the bag and providing a fluid tight and odour tight container.

For example, in an embodiment, the multiple layer sheet material comprises a sheet layer facing towards the interior of the bag, which inward facing sheet layer is a Polyethylene material for sealing the panel surfaces to each other, and a sheet layer facing outwards, which outwards facing sheet layer is a Polyethyleentereftalaat material, and a central layer comprising mostly a Nylon material, to enhance the barrier properties of the multiple layer sheet material.

The standing bag according to the invention essentially is a flexible pouch, configured to stand in an upright position on a support surface. According to the invention the collecting bag is furthermore provided with a collecting opening and a fitment for taking samples.

The collecting opening is adapted to enable urinating in the bag, i.e. has an opening wide enough to enable urinating in the bag. In an embodiment, the kit further comprises a funnel for cooperating with the collecting opening, to facilitate urinating in the collecting bag. In an embodiment, the funnel is provided in the form a blank of sheet material, preferably cardboard material, which blank is configured to be folded into a funnel. To thus enable flat packaging of the kit.

In an embodiment, the collecting opening is provided between top edges of the front panel and the back panel. In an alternative embodiment, the collecting opening is provided at a top corner of the collecting bag, i.e. where the side edges of the front panel and the back panel meet the top edges of the front panel and the back panel, which enables a more angled entry trajectory.

The collecting opening is configured to be opened and closed repeatedly to enable multiple donations, prevent spillage or odours from escaping the bag between donations, and to allow for the contends of the bag to be shaken prior to taking a sample.

In an embodiment, the fluid tight closure device is provided in the form of a zip lock opening. In such an embodiment, the bag is preferably provided with grip members, for example in the form of flaps that are part of the front and back panel, which grip members provide the user with additional grip for pulling the front and back panel away from each other to open zip lock opening.

In an embodiment, preferably in an embodiment in which the collecting opening is provided in the form of a zip lock, the kit further comprises an essentially Y-shaped bracket, which bracket comprises two parallel legs at one end and a grip at an opposite end, and wherein the bag is provided at the top edges of the front panel and the back panel with receiving channels for receiving those legs, such that when the legs are inserted into the receiving channels, the bag can be held at the grip and the collecting opening of the bag is held open and supported by the two legs of the Y-shaped bracket. The y-shaped bracket can be provided in a flat configuration, for example as a flat injection moulded object or folded out of metal wire, and thus allows for flat and compact packaging of the kit. At the same time it allows for a collecting bag that is flat and can be folded during storage and transport, but is provided with a wide collecting opening during use to facilitate donating urine in the bag.

In an embodiment, the collecting bag comprises a collecting opening member, preferably obtained by the injection moulding technique, which collecting opening member is sealed between the front panel and the back panel at the top edges thereof, and wherein the collecting opening of the bag is provided in the collecting opening member. Thus, the collecting opening member is defined by the collecting opening member, which in turn is sealed between the front and back panel of the bag. Providing an injection moulded collecting opening member allows for integrating the closure device, or parts thereof, in said member. For example, the member can be provided with screw thread for cooperating with a screw cap, or a hinged cap can be injection moulded as an integral part with the member.

In an embodiment, the fluid tight closure device can be configured as a stop or cap that is clicked, preferably screwed, into a closure position, in which closure position it seals of the collecting opening. Such a closure device is preferably combined with an injection moulded collecting member as disclosed above. For example, in an embodiment the collecting opening member and the stop are provided with screw thread or a bayonet fitting, for securing the stop in the collecting opening.

In an embodiment, the collecting opening member is injection moulded, and comprises:

a foot section, which foot section is configured to be sealed between the front panel and the back panel of the back, i.e. has sealing surfaces on opposite sides of a passage that defines at least part of the collecting opening;

a head section, located above the foot section, and preferably integrally injection moulded therewith, which head section has a base that flanges out, and has at least one circumferential wall on top of that base, which circumferential wall on its inside defines at least part of the collecting opening, and is on its outside provided with screw thread for cooperating with corresponding screw thread of a cap; and a cap, which cap is provided with inside screw thread to enable it to be screwed onto the head part, using the screw thread provided on the head section, to seal of the collecting opening.

The broadening of the base of the head provides the head with a wide collecting opening, while the collecting opening in the foot parts is relatively narrow, In such an embodiment, the wide collecting opening of the head section may function as a funnel for the narrower collecting opening of the foot section. Thus, the foot section can be compact, which facilitates sealing it between the front panel and the back panel of the bag, without hampering the collecting capabilities of the bag.

In a further embodiment, the head section is furthermore configured for receiving a funnel section, to further facilitate donating urine into the back through the comparatively narrow collecting opening in the foot of the collecting member.

In an embodiment, the collecting opening member is sealed between the front panel and the back panel at the top edges thereof and at a top corner of the bag, such that the collecting opening, defined by the collecting opening member, is at an angle with both the top edge and the side edge of the bag. Such an angled opening facilitates donating urine in the bag when holding it at the top or opposite corner, or even when the bag is in its free standing position on top of a table, a toilet lid, etc. In such an embodiment, a central axis of the collecting opening would extend at an angle with a vertical, preferably at an angle with the vertical of about 45 degrees.

According to the invention, the collecting bag comprises a female connector fitment adapted to connect to a sample end of an evacuated test tube to enable taking a urine sample from the urine deposited in the bag using the evacuated test tube. The fitment has a recess, i.e. a blind hole that matches the size and preferably the shape of the sample end of the air-evacuated test tube, into which the sample end of the evacuated test tube can be inserted.

It is submitted that evacuated test tubes are typically used for collecting samples of fluid. Such test tubes are provided with a pierceable closures, for example a rubber stopper, that can be pierced with a needle, or needle like piercing element, to pass fluid into the test tube. The vacuum draws the fluid into the test tube. A collecting bag according to the invention is configured to be used with these types of test tubes, at least one of which is part of the kit.

The female connector fitment is provided with a piercing member, located within its recess in a position to pierce a stopper or other pierceable closure of the air-evacuated tube when the sample end of the test tube is received with its sample end first into the recess. The size of the recess is adapted to enclose the needle like piercing element, such that it does not extend beyond an entry opening of the recess, preferably such that the entry opening of the recess is located at a distance from the tip of the piercing element, and thus shields the tip of the piercing element to prevent it from coming into contact with the fingers of a person by accident.

It is noted that because the fitment has a recess for receiving the sample end of the test tube, the fitment has a length in a direction parallel to a central axis of said recess. Furthermore, because the fitment is sealed to the front panel and/or the back panel it is provided with a sealing surface or sealing surfaces, that is, or are, sealed to part of the front panel or back panel.

In a preferred embodiment, the fitment is provided between the front panel and the back panel, and is sealed to the inside surface of the front panel and the back panel at their side edges or at their top edges. In such an embodiment, the fitment is provided with two sealing surfaces, one for sealing the fitment to the front panel and one for sealing the fitment to the back panel, which sealing surfaces are provided on opposite sides of the fitment, and substantially face away from each other.

In such an embodiment, the recess is located between the opposed sealing surfaces, which sealing surfaces extend in a lateral direction, i.e. in a direction substantially perpendicular to the length of the fitment, wherein length of the fitment is defined by a central axis of the recess. Thus, when the fitment is sealed between the front panel and the back panel, the sealing surfaces extends parallel to the surface of the front and back panel, and the recess extends in a direction essentially parallel to the surface of the front panel and the back panel and perpendicular to the side edges, or to the top edges, of the front panel and the back panel. Thus, the sample end of the test tube is inserted into the recess in a direction essentially parallel to the surface of the front panel and the back panel.

Furthermore, the sealing surfaces of the fitment have a length in a direction parallel to the central axis of the recess of the fitment, and a width in a direction perpendicular to this longitudinal direction.

It is noted that the fitment has two main dimensions, i.e. its width, determined by distance the sealing surfaces extend along the edge of the panels, and its length, determined by the depth of the recess for receiving the test tube. Its third dimension, the thickness, is small compared to its width and length. The thickness of the fitment is mainly determined by the diameter of the recess, and thus by the outside diameter of the test tube. Thus, when the fitment is provided between the front panel and the back panel, and is sealed to the inside surface of the front panel and the back panel, the fitment extends substantially parallel to the front panel and back panel of the collecting bag. This allows for a substantially flat bag, prior to use, which facilitates storage and transport.

In an alternative embodiment, the fitment is sealed in an opening in the front panel or the back panel, such that the entry opening of the recess faces away from the outside surface of the panel and the test tube is inserted in the recess in an insert direction substantially perpendicular to the outside surface of the front panel or back panel. In such an embodiment, the fitment has a main body defining the recess, and a flange extending around said main body, which flange provides a sealing surface extending in a direction perpendicular to a central axis of the recess. The fitment is sealed to either the front panel or the back panel of the bag. According to the invention the bag is thus provided with a fitment that enables taking a sample from the contents of the bag using a test tube, which fitment can simply be sealed to the front or back panel. This configuration does not allow for a compact, essentially flat bag, prior to use, since the length of the fitment extends in a direction perpendicular to the front and back panel.

In a further embodiment of a bag of a kit according to the invention, the collecting bag comprises a third panel, extending between the front panel and the back panel of the bag thus forming a side panel, and the fitment, having a flange providing a sealing surface extending perpendicular to the central axis of the recess, is sealed in an opening in this third panel. Thus, the length of the fitment extends parallel to the front panel and the back panel, and the fitment extends substantially parallel to the front panel and back panel of the collecting bag. This allows for a substantially flat bag, prior to use, which facilitates storage and transport, however, not as flat as when the fitment is configured to be sealed between the front panel and the back panel directly, i.e. to the inside surface of the front panel and the back panel.

In a preferred embodiment, the fitment is sealed between the front panel and the back panel, and comprises a recess having a length larger than the length of the sealing surfaces. In such an embodiment, the fitment preferably has a main body, comprising the recess, and lateral "wings" or "arms", extending on opposite sides of the mains body, which wings are provided with sealing surfaces on opposite sides thereof. Thus, the fitment, when seen in a direction substantially perpendicular to the front or back panel has a T-shaped or a +-shaped configuration.

In these embodiments the fitment is located between the front panel and the back panel. As was set out above, the fitment has two main dimensions, i.e. a length in a direction parallel to a central axis of the recess and a width perpendicular to said length and substantially parallel to the sealing surfaces of the fitment, preferably parallel to a virtual plane of symmetry provided between the sealing surfaces. The thickness of the fitment, in a direction perpendicular to both the length and the width of the fitment, is relatively limited, providing the fitment with an essentially flat configuration. Thus, the fitments main dimensions extend substantially parallel to the front panel and the back panel of the collecting back contributing to an overall flat configuration of the collecting bag.

In a further embodiment, the recess is substantially located within a contour of the bag, the recess having a central axis and having a length along said central axis, and at least 90% of the length of the recess is located within the contour of the bag, i.e. on the inside of the side edges or the top edges of the front and back panel, and less than 10% is located outside the contour of the back, i.e. on the outside of the side edges or top edges of the front panel and back panel.

In a further embodiment, the whole fitment is substantially located within a contour of the bag, the fitment having a longitudinal axis that coincides with a central axis of the recess, and wherein at least 90% of the length of the fitment is located within the contour of the bag, i.e. on the inside of the side edge of the front panel or back panel, and less than 10% is located outside the contour of the bag, i.e. on the outside of the side edges or top edges of the front panel and back panel. Thus, the fitment, when seen in a direction substantially perpendicular to the front or back panel has a T-shaped configuration.

By providing a fitment that is sealed between the front panel and the back panel, and that is configured to extend mainly within the contour of the bag, i.e. within the outline of the bag when seen in a direction perpendicular to the front panel or back panel, a compact bag is provided, i.e. a collecting bag with an essentially flat configuration prior to use, and allows for a collecting bag with an essentially rectangular contour, i.e. with no elements protruding beyond the side and/or top edges of the front panel and the back panel, when seen in a direction essentially perpendicular to the surface if the front panel and the back panel.

When the fitment is sealed to the front panel and to the back panel, and the recess is provided between the sealing surfaces, at least one of the sealing surfaces of the fitment is curved to thus enable front panel and the back panel to meet each other at the edge of the fitment. Preferably, both sealing surfaces are curved. Preferably, both sealing surfaces are curved and are symmetrical relative to a virtual plane of symmetry, which plane of symmetry comprises the central axis of the recess opening. By providing these symmetrical sealing surfaces, both front panel and back panel of the collecting bag are curved at the location of the fitment, and are transformed by the fitment in the same extend. Therefore the internal stresses in the bag, caused by the front panel and the back panel being curved by the sealing surfaces of the fitment, are more evenly distributed between the front and the back of the bag, which provides the bag with a more firm standing position.

Furthermore, when the fitment is sealed between the front panel and the back panel, the recess for receiving the sample end of the test tube is provided between the two sealing surfaces, such that when a sample end of the test tube is inserted into the recess, it is essentially inserted between the front panel and the back panel of the collecting bag. In such an embodiment, the user can engage the fitment at opposite sides, i.e. at the sealing surfaces, and thus hold the collecting bag at the fitment, even when the fitment does not extend beyond the contour of the bag. Thus holding the fitment provides the user with a secure grip of the bag. This is beneficial when inserting the sample end of the test tube into the recess since the piercing of the closure of the test tube requires some pushing force to be exerted onto the test tube while inserting it into the fitment.

In an embodiment, when the bag is in its standing position, the vertical distance between the inlet opening of the fitment and the top edges of the front panel and the back panel is larger than the vertical distance between the inlet opening of the fitment and the bottom edges of the front panel and the back panel, preferably is at least twice the vertical distance between the inlet opening of the fitment and the bottom edges of the front panel and the back panel. Thus, the fitment is located near the bottom panel, while allowing a person to take a sample while the collecting bag is in its standing position. Locating the inlet near the bottom panel allows for the inlet opening to be submerged, and thus for taking a sample, even when the bag is only partially filled.

In an embodiment, the connector fitment further comprises a flexible tube member, which tube member has an inlet end and an outlet end, which outlet end is connected to the inlet opening of the sample channel such that the tube member forms an extension of the sample channel, and wherein the tube member has a length such that when the bag is in its standing position, the inlet opening of the tube member is located near or at the bottom panel of the bag. When the standing bag is in its upright position, the end of the flexible tube member hangs down towards the bottom of the bag, so that communication between the bottom part section of the bag and the test tube is established when the test tube is inserted in the recess. Providing the flexible tube member thus allows a person to take a sample while the collecting bag is in its standing position, even when the bag is only partially filled. Such a configuration of the fitment is in particular beneficial when the fitment is located in the upper half or at the top of the standing bag, for example when the fitment is located between the top edges of the front panel and the back panel.

In an embodiment the fitment is located at the top of the bag, for example is located between the top edges of the front panel and the back panel, and the collecting bag comprises an collecting opening member which is sealed between the front panel and the back panel at the top edges thereof, and the collecting opening of the bag is provided in the collecting opening member. In such an embodiment, the female connector fitment is part, preferably an integral part, of the plastic collecting opening member. Therefore, only a single body, comprising both the fitment and the collecting opening, is to be sealed between a flexible front panel and back panel to provide a collecting bag according to the invention. Furthermore, in such an embodiment, the plastic collecting member at the top end of the bag may substantially mirror the bottom panel at the bottom end of the bag, such that the opposed sides of the panels, i.e. the opposite sides at which the front panel and the back panel meet each other and the bottom and top sides at which the front panel and the back panel are joint with a bottom panel and the collecting opening member respectively, run along similar trajectories, i.e. along a straight trajectory or along a curved trajectory respectively.

In an embodiment according to the invention the kit further comprises a packaging for holding and transporting the further components of the kit. In a preferred embodiment, the packaging comprises an envelope, preferably a postal envelope for distributing the kit by post.

The invention furthermore provides a female connector fitment for connecting with a sample end of an evacuated test tube, which connector fitment is adapted to be sealed by means of a sealing technique between film walls of a bag to enable taking a sample of fluid held in an interior of the bag using an evacuated test tube.

In an embodiment, a connector fitment according to the invention comprises:

a plastic member having a recess for receiving the sample end of the test tube, the recess having a central axis, which plastic member is provided with two lateral sealing wings located on opposite sides of the recess and extending in a direction perpendicular to the central axis of the recess, wherein the sealing wings support sealing surfaces for sealing the connector between film walls;

a piercing element, located within the confines of the connector port, for piercing a closure provided in the sample end of the test tube inserted into the connector port, which piercing element comprises a sample channel extending between an exit opening at the tip of the piercing element, and an entry opening at an exterior of the connector part, which entry opening is located in the interior of the bag when the connector part has been sealed between the wall panels of the bag, via which sample channel a liquid deposited in the interior of the bag can flow from the interior of the bag into a test tube having a sample end inserted into the connector part;

a flexible sealing sleeve, provided around the piercing element, which sealing sleeve seals the exit port to prevent leakage via the sample channel, and which sealing sleeve is strips up along the piercing element when the sample end of the test tube is inserted into the connector port and the piercing element pierces the closure provided in the sample end of the test tube.

In an embodiment of a connector fitment according to the invention, the sealing wings of the fitment have a frontal surface, for sealing the fitment to the inside surface of a front panel of a bag, and a back surface, for sealing the fitment to the inside surface of a back panel of a bag. The sealing surfaces are furthermore adapted to be sealed to the front and back panel along the sealing margins, disposed along the edges of the panels, at which the front and back panel are to be sealed to each other.

Preferably, the sealing surfaces of the connector fitment according to the invention are curved, with an entry opening of the recess located between the sealing surfaces and at a mid-section of those sealing surfaces, with the end sections of the sealing surfaces curving towards each other, such that the sealing surfaces meet each other at their ends.

In an embodiment of a connector fitment according to the invention, the cylindrical recess defines a central axis, and the connector is symmetric relative to a fictional central plane of symmetry, the plane of symmetry comprising said central axis.

Further objects, embodiments and elaborations of the apparatus and the method according to the invention will be apparent from the following description, in which the invention is further illustrated and elucidated on the basis of a number of exemplary embodiments, with reference to the drawings.

DETAILED DESCRIPTION

Figure 1:
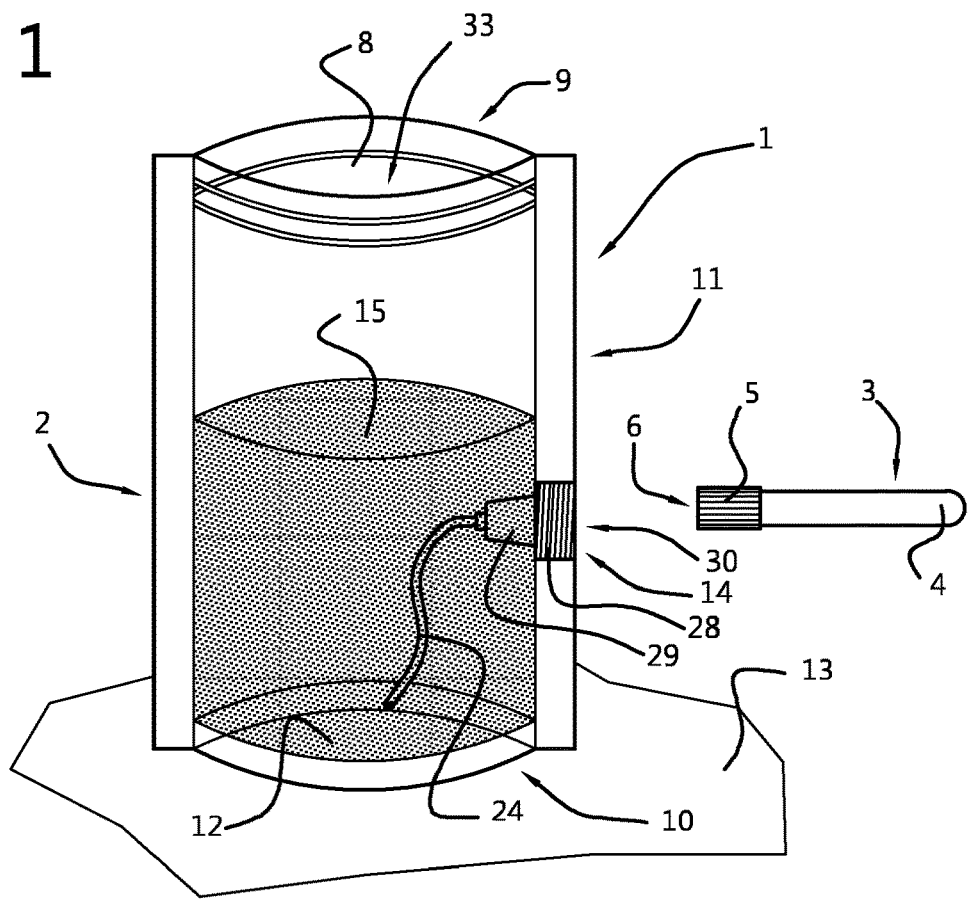
FIG. 1 shows a frontal view of a urine sample kit according to the invention.
Figure 2:
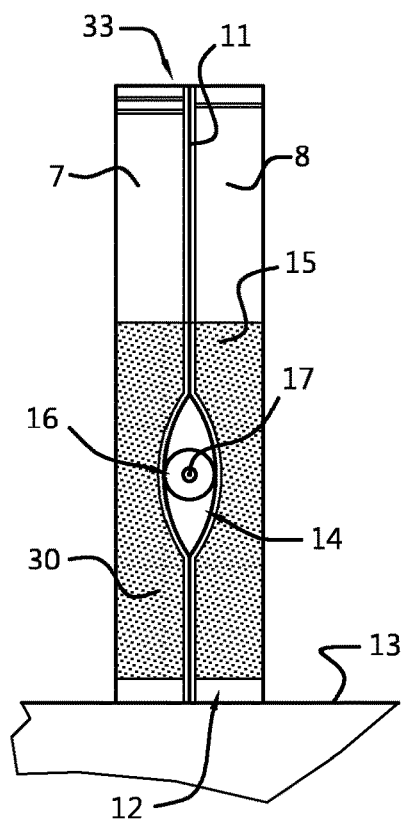
FIG. 2 shows a side view of the urine sample kit of FIG. 1.

FIG. 1 shows a urine sample kit 1 according to the invention, the kit 1 comprising a self-standing urine collecting bag 2 and an evacuated test tube 3. In the embodiment shown, the collecting bag 2 is partially filled with urine 15. FIG. 2 shows a side view of the bag of FIG. 1.

The evacuated test tube 3 has a bottom end 4 and an opposite sample end 5. The sample end 5 is provided with a pierceable closure 6.

The collecting bag 2 has a top portion and a bottom portion. The collecting bag 2 further comprises a front panel 7 and a back panel 8. The front panel 7 and the back panel 8 each have a top edge 9, a bottom edge 10, opposite side edges 11, an inside surface and an outside surface. The front panel 7 and back panel 8 meet each other at the opposite side edges 11 with their inside surfaces facing each other.

A bottom panel 12, located between the bottom ends of the front panel 7 and back panel 8. The bottom panel 12 provides support for the front panel and back panels so that, when filled with urine, the urine collection bag is self-supporting and can maintain a stable vertical standing position, as shown in FIG. 1, when resting on a substantially horizontal support surface 13.

The collecting bag is provided with a female connector fitment 14. The connector fitment 14 is adapted to connect to the sample end 5 of the evacuated test tube 3 to enable taking a urine sample from the urine 15 collected in the bag using the evacuated test tube 3

The top of the bag has a collecting opening 33 and fluid tight closure device is provided in the form of a zip lock opening. The bag is preferably provided with grip members, in the form of flaps extending along the length of the zip lock, which grip members provide the user with additional grip for pulling the front and back panel away from each other to open zip lock opening.

A female connector fitment 14 according to the invention is adapted to be sealed between to panels, preferably between a front panel and a back panel, of a collection bag, and to connect to a sample end 5 of an evacuated test tube 3 to enable taking a urine sample from the urine 15 deposited in the bag 2 using the evacuated test tube 3.

Figure 3:
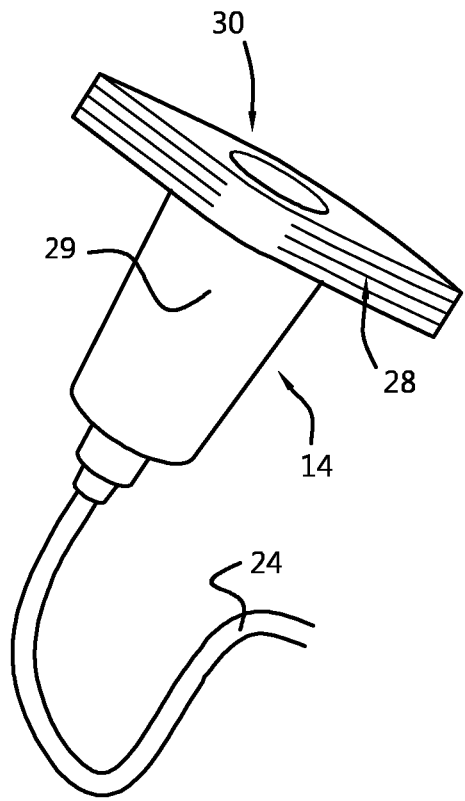
FIG. 3 shows a perspective side view of a female connector fitment for providing a bag of a kit according to the invention.
Figure 4:
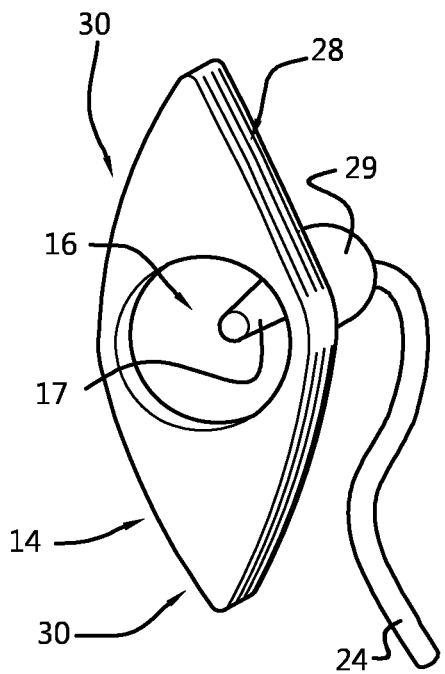
FIG. 4 shows a perspective frontal view of the fitment of FIG. 3.
Figure 5:
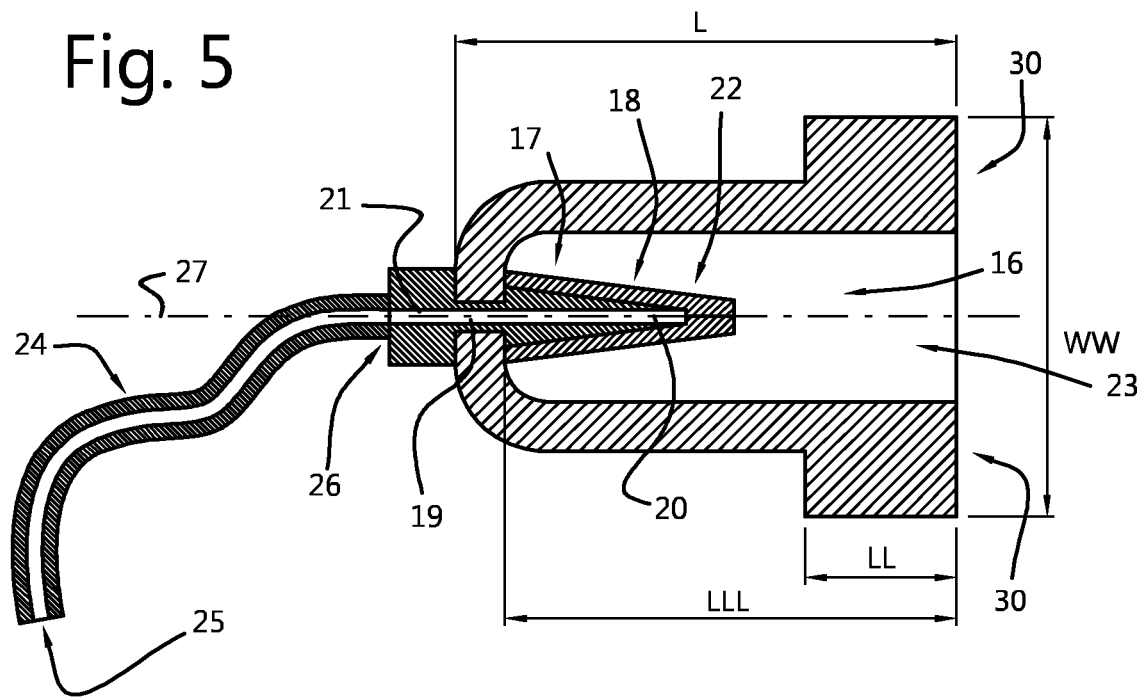
FIG. 5 shows a schematic side view in cross section of the fitment of FIG. 3.

FIGS. 3 and 4 show perspective views of the female connector fitment 14 for providing a bag of a kit according to the invention. FIG. 5 shows a schematic side view in cross section of the fitment.

The fitment 14 comprises a recess 16 for receiving the sample end 5 of the test tube 3. Within the recess 16, the fitment 14 is provided with a piercing member 17. The piercing member 17 is located within the confines of the recess 16 such that it does not extend outside the recess, which is clear from the side view shown in FIG. 1 and the cross section shown in FIG. 5.

The piercing member 17 has a tip 18 for piercing the pierceable closure 6 of the test tube 2 when the sample end 5 of the test tube 2 is inserted into the recess 16 of the female connector fitment 14.

The fitment 14 further comprises a sample channel 19 extending between an exit opening 20 at the tip of the piercing member, and an inlet opening 21 at a part of the connector fitment 14 located in the interior of the bag 2. Via the sample channel 19 urine 15 deposited in the interior of the bag 2 can flow from the interior of the bag into the test tube 3 having its sample end 5 inserted into the recess 16 of the connector fitment 14.

The fitment 14 further comprises a flexible sealing sleeve 22, provided around the piercing member 17. The sealing sleeve 22 seals the exit opening 20 to prevent leakage via the sample channel when the fitment is not connected with a test tube. When the sample end 5 of the test tube 3 is inserted into the recess 16, and the piercing member penetrates the pierceable closure of the test tube, the sealing sleeve 22 strips up, i.e. pushed by the pierceable closure, along the piercing member 17 to unseal the exit opening 20.

According to the invention, in the exemplary embodiment shown in FIG. 1, the connector fitment 14 is sealed by means of a sealing technique to the front panel 7 and back panel 8 of the collecting bag.

In the embodiment shown, the fitment 14 is provided at a height above the bottom panel 12, such that the insert opening 23 of the recess 16 faces outward and the sample end 5 of the test tube 3 can be inserted into the recess 16, and can be removed from the recess 16, while the bag 2 is in its standing position.

In the exemplary embodiment shown, the fitment furthermore comprises a flexible tube member 24. The tube member 24 has an inlet end 25 and an outlet end 26. The outlet end 26 is connected to the inlet opening 21 of the sample channel 19 such that the tube member 24 forms an extension of the sample channel. The tube member 24 has a length such that when the bag 2 is in its standing position, as depicted in FIG. 1, the inlet opening 25 of the tube member 24 is located at the bottom panel 12 of the bag so that fluid communication between the bottom part section of the bag and the test tube is established when the sample end of the test tube is inserted in the recess. In an alternative embodiment, the fitment does not have a flexible tube member.

It is noted that because the fitment 14 has a recess 16 for receiving the sample end 5 of the test tube 3, the fitment has a length L in a direction parallel to a central axis 27 of said recess. Furthermore, because the fitment is sealed to the front panel and/or the back panel it is provided with a sealing surface that is sealed to part of the front panel or back panel. In the particular embodiment shown, the fitment 14 is provided with two sealing surfaces 28, one for sealing the fitment to the front panel and one for sealing the fitment to the back panel, which sealing surfaces are provided on opposite sides of the fitment, and substantially face away from each other.

In the preferred embodiment shown, the sealing surfaces 28 extend in a direction substantially perpendicular to the length L of the fitment 14, such that, when the fitment is sealed in the bag as shown in FIG. 1, the recess 16 extends in a direction essentially perpendicular to the side edges of the front panel and the back panel.

Furthermore, the sealing surfaces 28 have a length LL in a direction parallel to the central axis 27 of the recess 16 of the fitment 14, and a width WW in a direction perpendicular to this longitudinal direction. Thus, the width W of the sealing surfaces 28 extends parallel to surface of the front and back panel, when the fitment is sealed to the front and back panel.

In the exemplary embodiment shown, the fitment 14 comprises a recess 16 having a length, or depth, LLL larger than the length LL of the sealing surfaces. Furthermore, the fitment has a main body 29 comprising the recess 16, and lateral wings 30. The lateral wings 30 extend on opposite sides of the main body 29, and on opposite sides support the sealing surfaces 28. Thus, in the preferred embodiment shown, the fitment 14, when seen in a directions substantially perpendicular to the front or back panel, has a T-shaped configuration. Such a configuration enables the fitment to be located within the contour of the bag, which is clear from for example FIG. 1, and thus allows for a compact bag.

In the exemplary embodiment shown, the fitment 14 thus has two main dimensions, i.e. a length L, in a direction parallel to a central axis 27 of the recess 16, and a width VWV, similar to the width WW of the sealing surfaces 28. The thickness T of the fitment, in a direction perpendicular to both the length and the width of the fitment, is relatively limited, providing the fitment with an essentially flat configuration. Thus, the fitments main dimensions extend substantially parallel to the front panel and the back panel of the collecting back contributing to an overall flat configuration of the collecting bag.

The T-shaped configuration of the fitment shown allows for the fitment being sealed into the back with its recess substantially located within a contour of the bag. As is for example clear from FIG. 1, at least 90% of the length of the recess is located within the contour of the bag, i.e. on the inside of the side edges or the top edges of the front and back panel, and less than 10% is located outside the contour of the back, i.e. on the outside of the side edges or top edges of the front panel and back panel.

Furthermore, in the preferred embodiment shown, not only more than 90% of the recess is located within the contour of the bag, also at least 90% of the length of the fitment is located within the contour of the bag, i.e. on the inside of the side edge of the front panel or back panel, and less than 10% is located outside the contour of the bag, i.e. on the outside of the side edges or top edges of the front panel and back panel.

By providing a fitment that is sealed between the font panel and the back panel, and that is configured to extend mainly within the contour of the bag, i.e. within the outline of the bag when seen in a direction perpendicular to the front panel or back panel, a compact bag is provided, i.e. a collecting bag with an essentially flat configuration prior to use, and allows for a collecting bag with an essentially rectangular contour, i.e. with no elements protruding beyond the side and/or top edges of the front panel and the back panel, when seen in a direction essentially perpendicular to the surface if the front panel and the back panel.

At least one of the sealing surfaces of a fitment according to the invention is curved to thus enable front panel and the back panel to meet each other at the edge of the fitment. In the preferred embodiment shown, both sealing surfaces 28 are curved. Furthermore, both sealing surfaces 28 are curved and are symmetrical relative to a virtual plane of symmetry, which plane of symmetry comprises the central axis of the recess opening.

Furthermore, when the fitment is sealed between the front panel and the back panel, the recess for receiving the sample end of the test tube is provided between the two sealing surfaces, such that when a sample end of the test tube is inserted into the recess, it is essentially inserted between the front panel and the back panel of the collecting bag. In such an embodiment, the user can engage the fitment at opposite sides and thus hold the collecting bag at the fitment, even when the fitment is does not extend beyond the contour of the bag. Thus holding the fitment is beneficial when inserting the sample end of the test tube into the recess, since the piercing of the closure of the test tube requires a firm grip of the fitment.

Figure 6:
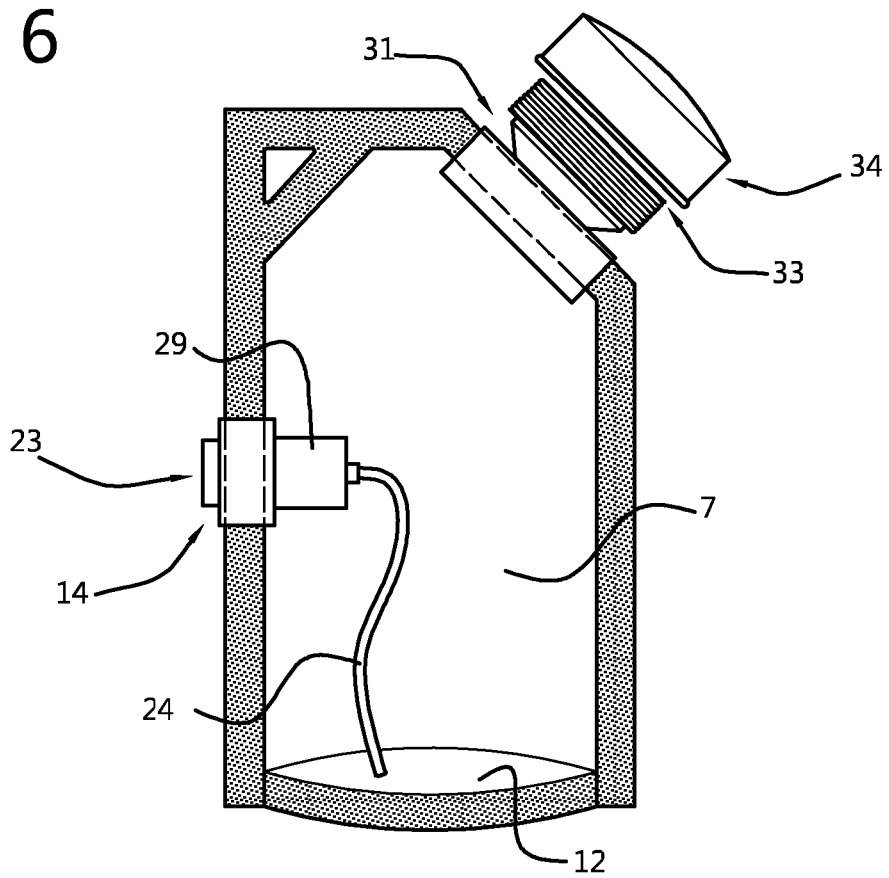
FIG. 6 shows an alternative embodiment of a bag for providing a kit according to the invention.
Figure 7:
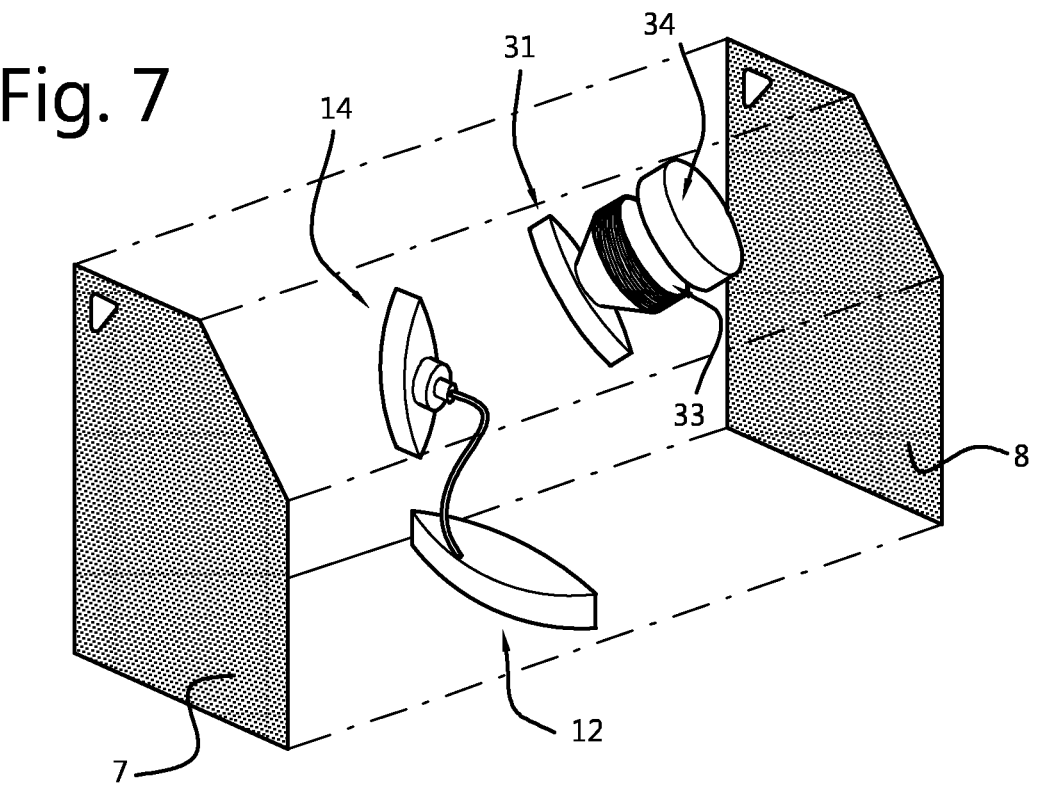
FIG. 7 shows an exploded view of the bag of FIG. 6.

FIG. 6 shows an alternative embodiment of a bag for providing a kit according to the invention. FIG. 7 shows an exploded view of the bag, in which the front panel, the back panel and the bottom panel are depicted as separate components.

Similar to the bag shown in FIG. 1, the stand-up bag shown in FIG. 6 is made of a heat-sealable or weldable plastic sheet material and adapted to contain liquid. The exemplary embodiment shown comprises two substantially rectangular sheet elements, forming the front panel and the back panel, and a foldable bottom wall sheet element acting as a stand-up support bottom. The sheet elements are sealed to each other along their sides, the bottom panel being sealed to the front and back panel such that it lies between said panels.

The collecting bag shown in FIG. 6 differs from the one shown in FIG. 1 in that it comprises a plastic collecting opening member 31, obtained by the injection moulding technique. The collecting opening member 31 is sealed between the front panel 7 and the back panel 8 at the top edges thereof, more in particular at a top corner, and the collecting opening of the bag is provided in the collecting opening member.

A fluid tight closure device 32 is provided in the form of a cap. Cap 32 and member 31 are provided with corresponding screw thread, to enable the cap to be screwed into a closure position onto the member, in which closure position the cap seals of the collecting opening. It is noted that this type of opening is preferred over a closure device comprising a zip lock, since the latter is difficult to open and close gradually, and more prone to generate shocks during the process of opening the bag and thus to spilling already collected urine.

In an embodiment according to the invention the kit further comprises a packaging for holding and transporting the further components of the kit. In a preferred embodiment, the packaging comprises an envelope, preferably a postal envelope for distributing the kit by post.

Figure 8:
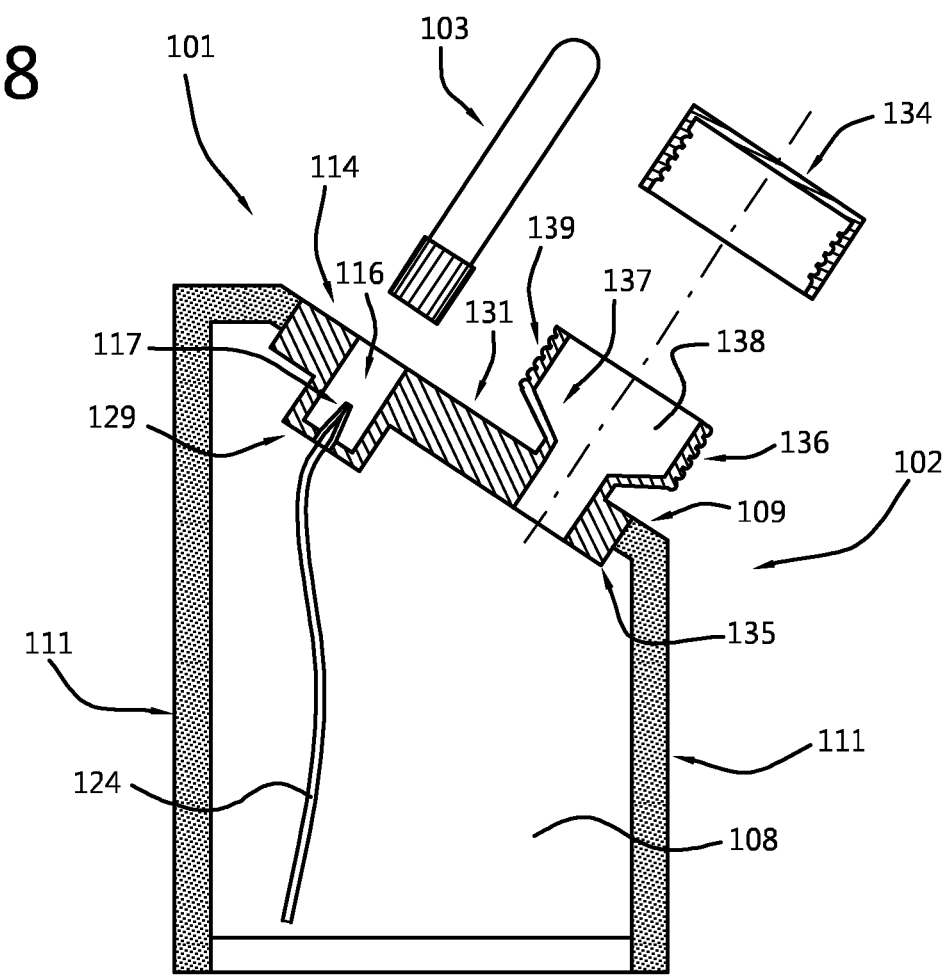
FIG. 8 shows a side view in cross section of an alternative urine collecting bag of a urine sample kit according to the invention.

FIG. 8 shows a side view in cross section of an alternative urine collecting bag 102 of a urine sample kit 101 according to the invention.

The collecting bag 102 comprises an injection moulded collecting opening member 131. The collecting opening member 131 is sealed between a front panel and a back panel 108 at the top edges 109 thereof. The collecting opening 133 of the bag is provided in the collecting opening member 131. Thus, the collecting opening 133 is defined by the collecting opening member 131, which in turn is sealed between the front panel and back panel 108 of the bag 102. A fluid tight closure device is provided in the form of a cap 134 can be screwed into a closure position onto the collecting opening member 131, in which closure position it seals of the collecting opening 133.

In the embodiment shown, the collecting opening member 131 is sealed between the front panel and the back panel 108 at the top edges 109 thereof and at a top corner of the bag, such that the collecting opening 133, defined by the collecting opening member 131, is at an angle with both the top edges 109 and the side edges 111 of the bag 102. Such an angled opening facilitates donating urine in the bag when holding it at the top or opposite corner, or even when the bag is in its free standing position on top of a table, a toilet lid, etc. In such an embodiment, a central axis of the collecting opening would extend at an angle with a vertical, preferably at an angle with the vertical of about 45 degrees.

In the embodiment shown, the collecting opening member 131 comprises:

a foot section 135, which foot section is configured to be sealed between the front panel and the back panel 108 of the bag 102, i.e. has sealing surfaces on opposite sides of a passage that defines at least part of the collecting opening 133;

a head section 136, located above the foot section 135, and integrally injection moulded therewith, which head section 136 has a base 137 that flanges out, and has a circumferential wall 138 on top of that base, which circumferential wall 138 on its inside defines at least part of the collecting opening 133, and is on its outside provided with screw thread 139 for cooperating with corresponding screw thread 139 of the cap 134.

The cap 134 is provided with inside screw thread 139 to enable it to be screwed onto the head section 136, using the screw thread 139 provided on the head section 136, to seal of the collecting opening 133.

The broadening of the base 137 of the head section 136 provides the head section with a wide collecting opening 133, while the part of the collecting opening 133 in the foot section 135 of the collecting member 131 is relatively narrow. The wide collecting opening of the head section may function as a funnel for the narrower collecting opening of the foot section. Thus, the foot section can be compact, which facilitates sealing it between the front panel and the back panel of the bag, without hampering the collecting capabilities of the bag.

Preferably, the head section is furthermore configured for receiving a funnel, to further facilitate donating urine into the back through the comparatively narrow collecting opening in the foot of the collecting member.

In the embodiment shown, the female connector fitment 114 is located at the top of the bag 102, and is an integral part of the injection moulded collecting opening member 131. That is, the body defining the recess 116 is an integral part of the injection moulded collecting opening member 131. It is noted that the piercing member 117 is a separate component that is inserted during the assembly process.

By combining the fitment 114, or at least part thereof, in a single body shared with the collecting opening member 131, only a single body, comprising both the fitment and the collecting opening, is to be sealed between a flexible front panel and back panel to provide a collecting bag according to the invention.

Furthermore, the collecting opening member 131 at the top end of the bag 102 substantially mirrors the shape of the bottom panel at the bottom end of the bag. Thus, the opposite sides at which the front panel and the back panel meet each other run along similar trajectories, i.e. along a straight trajectory, and the bottom and top sides of the front panel and the back panel, at which the front panel and the back panel are joint with a bottom panel and the collecting opening member respectively, run along similar trajectories, i.e. along a curved trajectory respectively.

In an embodiment according to the invention the kit further comprises a packaging for holding and transporting the further components of the kit. In a preferred embodiment, the packaging comprises an envelope, preferably a postal envelope for distributing the kit by post.

Figure 9:
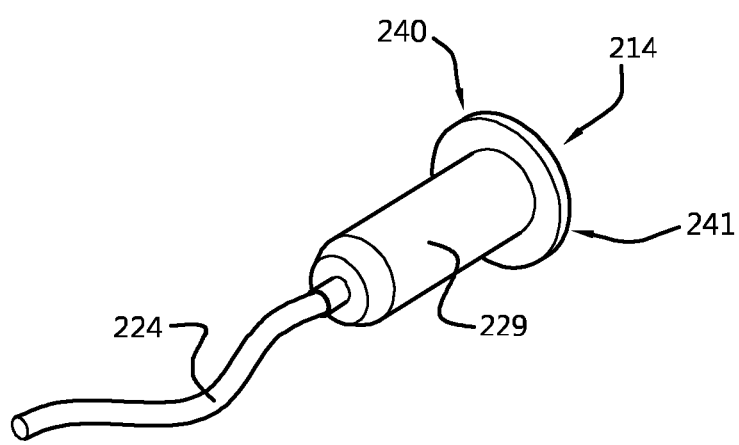
FIG. 9 shows a perspective side view of an alternative female connector fitment for providing a bag of a kit for collecting and sampling urine.

FIG. 9 shows a perspective side view of an alternative female connector fitment 204 for providing a bag of a kit for collecting and sampling urine. The female connector fitment 204 has a main body 229 defining the 216 recess for receiving the sample end of a test tube, and a flange 140 extending around said main body 229, which flange provides a single sealing surface 141 extending in a direction perpendicular to a central axis of the recess 216, for sealing the fitment 204 in an opening in a panel of the collecting bag.

Figure 10:
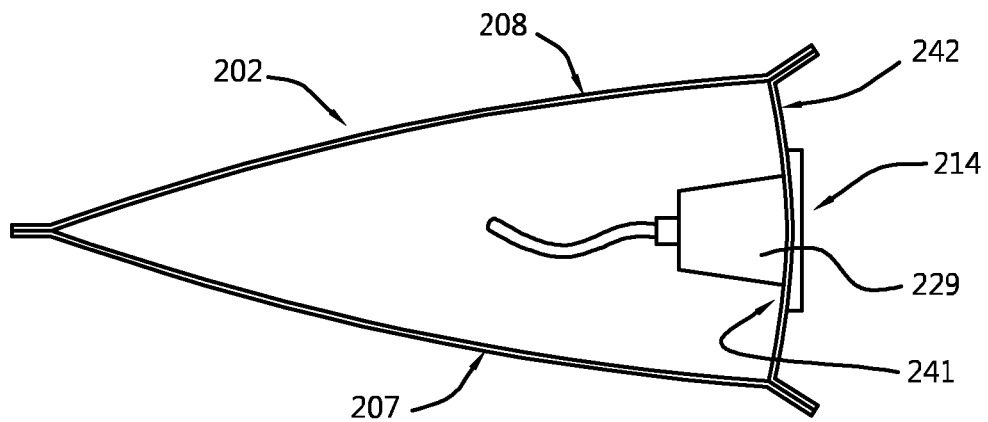
FIG. 10 a top view in cross section of an alternative urine collecting bag provided with the female connector fitment of FIG. 9.

FIG. 10 a top view in cross section of an alternative urine collecting bag 202 provided with the female connector fitment 204 of FIG. 9. The collecting bag 202 comprises a third panel 242, extending between the front panel 207 and the back panel 208 of the bag 202, thus forming a side panel. The fitment 204 is sealed in an opening in this third panel 242. It is noted that the third panel 242 has a width substantially smaller than the width of the front panel 207 and the back panel 208, i.e. a width less than one third the width of the front panel and the back panel. Thus, the length of the fitment 204 extends substantially parallel to the front panel 207 and back panel 209 of the collecting bag 202.

In an alternative embodiment, the urine collecting bag comprises a front panel and a back panel which meet each other on opposite sides. In such a bag, this type of fitment is sealed in an opening in either the front panel or the back panel of the bag. According to the invention the bag is thus provided with a fitment that enables taking a sample from the contents of the bag using a test tube, which fitment can simply be sealed to the front or back panel.

REFERENCE SIGNS 01 kit
02 self-standing urine collecting bag
03 evacuated test tube
04 bottom end test tube
05 sample end test tube
06 pierceable closure test tube
07 front panel collecting bag
08 back panel collecting bag
09 top edge front and back panel
10 bottom edge front and back panel
11 side edges front and back panel 12 bottom panel
13 horizontal support surface
14 connector fitment
15 collected urine
16 recess
17 piercing member
18 tip piercing member
19 sample channel connector fitment
20 exit opening sample channel
21 inlet opening sample channel
22 sealing sleeve
23 insert opening of the recess
24 flexible tube member fitment
25 inlet end tube member
26 outlet end tube member
27 central axis recess
28 sealing surfaces fitment
29 main body fitment
30 lateral wings fitment
31 collecting opening member
32 fluid tight closure device
33 collecting opening
34 cap
101 kit
102 self-standing urine collecting bag
103 evacuated test tube
108 back panel collecting bag
109 top edge front and back panel
111 side edges front and back panel
113 horizontal support surface
114 connector fitment
116 recess
117 piercing member
129 main body fitment
131 collecting opening member
132 fluid tight closure device
133 collecting opening
134 cap
135 foot section
136 head section
137 base head section
138 circumferential wall head section
139 screw thread
202 self-standing urine collecting bag
207 front panel collecting bag
208 back panel collecting bag
214 connector fitment
216 recess
229 main body fitment
240 flange alternative fitment
241 sealing surface flange
242 third panel
L length fitment in a direction parallel to a central axis of the recess
LL length of the sealing surfaces
LLL length of recess
WW width of the sealing surfaces
T thickness of fitment

The invention claimed is:
1. A urine collecting and sample kit, said kit comprising:
a self-standing urine collecting bag, having a top portion, a bottom portion and an interior; and
an evacuated test tube having a bottom end and an opposite sample end, the sample end being provided with a pierceable closure,
wherein the collecting bag comprises:
a front panel and a back panel, the front panel and the back panel each having a top edge, a bottom edge, opposite side edges, an inside surface and an outside surface, the front panel and the back panel meeting each other at the opposite side edges with their the inside surfaces facing each other;
a collecting opening adapted to enable urinating in the bag, the collecting opening being located at the top portion of the collection collecting bag, and the collecting opening being provided with a fluid tight closure device for repeatedly repeated fluid tight sealing of the collecting opening;
a bottom panel, located between the front panel and the back panel at the bottom end portion of the bag, the bottom panel providing support for the front panel and the back panels panel so that, when filled with urine, the urine collection collecting bag is self-supporting and can maintain a stable vertical standing position when resting on a substantially horizontal support surface; and
a female connector fitment adapted to connect to the sample end of the evacuated test tube to enable taking a urine sample from the urine deposited in the bag using the evacuated test tube, the fitment comprising:
a recess for receiving the sample end of the test tube, the recess having an insert opening for inserting the sample end into the recess, an entry section and a bottom section;
a piercing member, located within the confines of the recess such that it the piercing member does not extend outside said recess, the piercing member having a tip for piercing the pierceable closure of the test tube when the sample end of said test tube is inserted into the recess of the female connector fitment;
a sample channel extending between an exit opening at the tip of the piercing member, and an inlet opening at a part of the connector fitment located in the interior of the bag, via which sample channel the urine deposited in the interior of the bag can flow from the interior of the bag into the test tube having the sample end inserted into the female connector part fitment; and
a flexible sealing sleeve, provided around the piercing member, the sealing sleeve sealing the exit opening to prevent leakage via the sample channel, and the sealing sleeve stripping up along the piercing element when the sample end of the test tube is inserted into the recess to unseal the exit opening,
wherein the female connector fitment is located between the front panel and the back panel, has two sealing surfaces, and is sealed by a sealing technique with a first sealing surface of the two sealing surfaces to the inside surfaces of the front panel and a second sealing surface of the two sealing surfaces to the inside surface of the back panel such that the insert opening of the fitment faces outward and the sample end of the test tube can be inserted into the recess and be removed from the recess while the bag is in the standing position,
wherein the female connector fitment has a sealing part provided with the sealing surfaces and a bottom part provided with the inlet opening of the sample channel,
wherein the entry section of the recess extends through the sealing part of the female connector fitment, and the two sealing surfaces are located on opposite sides of the entry section of the recess, and wherein the bottom section of the recess is comprised in the bottom part of the female connector fitment, and is located in the interior of the bag.

2. The kit according to claim 1, wherein the female connector fitment is sealed to the inside surfaces of the front panel and the back panel at side edges or the top edges of the front panel and the back panel.

3. The kit according to claim 1, wherein the recess is substantially located within a contour of the bag, the recess having a central axis and having a length along said central axis, and wherein at least 90% of the length of the recess is located within the contour of the bag, and less than 10% is located outside the contour of the bag.

4. The kit according to claim 1, wherein the fitment is substantially located within a contour of the bag, the fitment having a longitudinal axis that coincides with a central axis of the recess, and wherein at least 90% of the length of the fitment is located within the contour of the bag, and less than 10% is located outside the contour of the bag.

5. The kit according to claim 1, wherein, when the bag is in the standing position, the a vertical distance between the inlet opening of the fitment and the top edges of the front panel and the back panel is larger than the vertical distance between the inlet opening of the fitment and the bottom edges of the front panel and the back panel.

6. The kit according to claim 1, wherein the fitment is located between the top edges of the front panel and the back panel.

7. The kit according to claim 1, wherein the collecting bag comprises a collecting opening member, the collecting opening member being sealed between the front panel and the back panel at the top edges thereof, and wherein the collecting opening of the bag is provided in the collecting opening member.

8. The kit according to claim 1, wherein the closure device comprises a stop, and wherein the collecting opening member and the stop are provided with a screw thread or a bayonet closure, for securing the stop in the collecting opening.

9. The kit according to claim 1, wherein the collecting bag comprises a collecting opening member, the collecting opening member being sealed between the front panel and the back panel at the top edges thereof, and
wherein the collecting opening of the bag is provided in the collecting opening member,
wherein the closure device comprise a stop, and
wherein the collecting opening member and the stop are provided with a screw thread or a bayonet closure, for securing the stop in the collecting opening, and
wherein the female connector fitment is part of the plastic collecting opening member.

10. The kit according to claim 1, wherein the kit further comprises a funnel.

11. The kit according to claim 1, wherein the kit further comprises a Y-shaped bracket, the bracket comprising two parallel legs at one end and a grip at an opposite end, and
wherein the bag is provided at the top edges of the front panel and the back panel with receiving channels for receiving the two legs, such that when the two legs are inserted into the receiving channels, the bag can be held at the grip and the collecting opening of the bag is held open between the two legs.

12. The kit according to claim 1, wherein the front panel, the back panel and the bottom panel of the bag are made of a foldable plastic sheet material.

13. The kit according to claim 1, wherein the kit further comprises a packaging for holding and transporting the further components of the kit.

14. A female The female connector fitment adapted to provide a collecting bag according to claim 1, the fitment being adapted to be sealed between two panels of the collection collecting bag, and to connect to a to the sample end of an of the evacuated test tube to enable taking a urine the urine sample from the urine deposited in the bag using the evacuated test tube.

15. A method for obtaining a urine the urine sample, the method comprising:
providing the kit according to claim 1; and
obtaining the test tube comprising a urine the urine sample for analysing said urine sample.

16. The kit according to claim 1, wherein the connector fitment further comprises a flexible tube member, which tube member has an inlet end and an outlet end, which outlet end is connected to the inlet opening of the sample channel such that the tube member forms an extension of the sample channel, and wherein the tube member has a length such that when the back is in its standing position, the inlet end of the tube member is located near or at the bottom panel of the bag.

* * * * *